US010544398B2

(12) United States Patent
Beltrán Pavez et al.

(10) Patent No.: US 10,544,398 B2
(45) Date of Patent: Jan. 28, 2020

(54) PLASMIDS AND METHOD FOR OBTAINING VIRAL PARTICLES

(71) Applicant: UNIVERSIDAD DE SANTIAGO DE CHILE, Santiago (CL)

(72) Inventors: Carolina Beltrán Pavez, Santiago (CL); Marcelo Cortez San Martin, Santiago (CL); Eugenio Spencer Ossa, Santiago (CL); Carolina Tambley Zamorano, Santiago (CL); Daniela Toro Ascuy, Santiago (CL)

(73) Assignee: UNIVERSIDAD DE SANTIAGO DE CHILE, Santiago (CL)

( * ) Notice: Subject to any disclaimer, the term of this patent is extended or adjusted under 35 U.S.C. 154(b) by 0 days.

(21) Appl. No.: 15/528,328

(22) PCT Filed: Jan. 6, 2016

(86) PCT No.: PCT/CL2016/050002

§ 371 (c)(1),
(2) Date: May 19, 2017

(87) PCT Pub. No.: WO2016/077938

PCT Pub. Date: May 26, 2016

(65) Prior Publication Data

US 2018/0030416 A1 Feb. 1, 2018

(30) Foreign Application Priority Data

Nov. 20, 2014 (CL) .................................. 3146-2014

(51) Int. Cl.

*C12N 7/00* (2006.01)
*C12N 15/86* (2006.01)
*C12N 15/85* (2006.01)

(52) U.S. Cl.

CPC ............... *C12N 7/00* (2013.01); *C12N 15/85* (2013.01); *C12N 15/86* (2013.01); *C12N 2760/16021* (2013.01); *C12N 2760/16022* (2013.01); *C12N 2760/16034* (2013.01); *C12N 2760/16043* (2013.01); *C12N 2760/16051* (2013.01); *C12N 2760/16151* (2013.01); *C12N 2760/16152* (2013.01); *C12N 2800/107* (2013.01); *C12N 2830/80* (2013.01)

(58) Field of Classification Search

None

See application file for complete search history.

(56) References Cited

FOREIGN PATENT DOCUMENTS

| | | | |
|---|---|---|---|
| WO | 0104333 | A1 | 1/2001 |
| WO | 2007144773 | A2 | 12/2007 |

OTHER PUBLICATIONS pTriEx™ System Manual (2011).*

International Search Report for International Application No. PCT/CL2016/050002, dated Mar. 18, 2016, 6 pages.

Neumann, et al. "Generation of influenza A viruses entirely from cloned cDNAs", Proc. Natl. Acad. Sci. USA, vol. 96, Aug. 1999, pp. 9345-9350.

Engelhardt, "Many ways to make an influenza virus—review of influenza virus reverse genetics methods", May 2013 7(3): 249-256.

Biacchesi, "The reverse genetics applied to fish RNA viruses", Veterinary Research, 2011, 42(1):12, 14 pages.

Cottet et al, "Bioinformatic Analysis of the Genome of Infectious Salmon Anemia Virus Associated with Outbreaks with High Mortality in Chile", J. Virol., 2010, 84:11916-11928.

Toro-Ascuy, et al. "Development of a Reverse Genetic System for Infectious Salmon Anemia Virus: Rescue of Recombinant Fluorescent Virus by Using Salmon Internal Transcribed Spacer Region 1 as a Novel Promoter", Appl. Environ. Microbiol. Feb. 2015; 81(4): 1210-24.

GenBank: AF201312.1 Salmo salar internal transcribed spacer 1, complete sequence.

* cited by examiner

*Primary Examiner* — Nancy J Leith

(74) *Attorney, Agent, or Firm* — Hoffman Warnick LLC

(57) ABSTRACT

The present invention describes a viral RNA expression plasmid and a method for obtaining viral particles based on the plasmids comprising transfecting animal cells with an expression vector or a set of expression vectors capable of expressing a nucleoprotein and RNA-dependent polymerase RNA; and transfecting the animal cell with an expression vector or a set of expression vectors with nucleotide sequences encoding recombinant RNA molecules.

13 Claims, 5 Drawing Sheets

Specification includes a Sequence Listing.

SEQUENCE LISTING

<160> NUMBER OF SEQ ID NOS: 10

<210> SEQ ID NO 1
<211> LENGTH: 577
<212> TYPE: DNA
<213> ORGANISM: Salmo salar

<400> SEQUENCE: 1
gctagcacgg gtttgccacc cgccggcatg gggctgcgct ccacaaacca aactctgctg 60
tgggtcgggt agggtagggg gctcacgcct cccgcctctc ccttccctcg gcgcgggtga 120
actggtccta gcccggttcc ccgcagttcc tttttgcctg ggatgcgccc aactggctcc 180
atcccctttc cccgttaggc acggctagat gacgcaccga tgggtgggtg tgtaggccgc 240
taccgagggg actgggggtg tccggtgaac cgggacttcc cgaaatggtc tcacattttt 300
aagcggcttg agtatcaccc agtatcttcg cgcggcactg ggaacccagt caaccgctct 360
gcgccccggc gcaggcgggg gtttaatgtc tccccggccc caccggcgct tcggcgacgg 420
cggcagagga gcacccggag gcccccataa agttaaacct acctgtcttt gaactatgac 480
ctctcgctct ggcgaagggc gggcagagga acggagggca acctcccatc tctgccttag 540
cctatagcct ctgcgtaaaa ctggacaaaa aagagta 577

<210> SEQ ID NO 2
<211> LENGTH: 44
<212> TYPE: DNA
<213> ORGANISM: Escherichia coli

<400> SEQUENCE: 2
ttttactctg atgaggcctt cgggccgaaa cggtgaaagc cgta 44

<210> SEQ ID NO 3
<211> LENGTH: 24
<212> TYPE: DNA
<213> ORGANISM: unknown
<220> FEATURE:
<223> OTHER INFORMATION: species unknown

<400> SEQUENCE: 3
agaagagccc ggactcgctc ttct 24

<210> SEQ ID NO 4
<211> LENGTH: 84
<212> TYPE: DNA
<213> ORGANISM: Hepatitis D virus

<400> SEQUENCE: 4
ggccggcatg gtcccagcct cctcgctggc gccggctggg caacattccg aggggaccgt 60
cccctcggta atggcgaatg ggac 84

<210> SEQ ID NO 5
<211> LENGTH: 163
<212> TYPE: DNA
<213> ORGANISM: Oryctolagus sp.

<400> SEQUENCE: 5
gatctttttc cctctgccaa aaattatggg gacatcatga agccccttga gcatctgact 60
tctggctaat aaaggaaatt tattttcatt gcaatagtgt gttggaattt tttgtgtctc 120
tcactcggaa ggacatatgg gagggcaaat catttaagtc gac 163

<210> SEQ ID NO 6
<211> LENGTH: 893
<212> TYPE: DNA
<213> ORGANISM: Infectious salmon anemia virus

<400> SEQUENCE: 6
gctagcacgg gtttgccacc cgccggcatg gggctgcgct ccacaaacca aactctgctg 60
tgggtcgggt agggtagggg gctcacgcct cccgcctctc ccttccctcg gcgcgggtga 120
actggtccta gcccggttcc ccgcagttcc tttttgcctg ggatgcgccc aactggctcc 180
atcccctttc cccgttaggc acggctagat gacgcaccga tgggtgggtg tgtaggccgc 240
taccgagggg actgggggtg tccggtgaac cgggacttcc cgaaatggtc tcacattttt 300
aagcggcttg agtatcaccc agtatcttcg cgcggcactg ggaacccagt caaccgctct 360
gcgccccggc gcaggcgggg gtttaatgtc tccccggccc caccggcgct tcggcgacgg 420
cggcagagga gcacccggag gcccccataa agttaaacct acctgtcttt gaactatgac 480
ctctcgctct ggcgaagggc gggcagagga acggagggca acctcccatc tctgccttag 540
cctatagcct ctgcgtaaaa ctggacaaaa aagagtattt ttactctgat gaggccttcg 600
ggccgaaacg gtgaaagccg taagaagagc ccggactcgc tcttctggcc ggcatggtcc 660
cagcctcctc gctggcgccg gctgggcaac attccgaggg gaccgtcccc tcggtaatgg 720

-continued

```
cgaatgggac gatctttttc cctctgccaa aaattatggg gacatcatga agccccttga    780

gcatctgact tctggctaat aaaggaaatt tattttcatt gcaatagtgt gttggaattt    840

tttgtgtctc tcactcggaa ggacatatgg gagggcaaat catttaagtc gac           893


<210> SEQ ID NO 7
<211> LENGTH: 2169
<212> TYPE: DNA
<213> ORGANISM: Infectious salmon anemia virus

<400> SEQUENCE: 7

atggacttta tatcagaaaa cacgatcagc gacaaaacca cgctagaaga actgaaaaat     60

gctactttat tccaagttac taaagtagac gacagggact gtctaaaagc aagaagaata    120

tgtaatgcac ctaaagggca ctgggctggt ctaatggaaa aagccaaggc aatgggagac    180

ccaactgaag aggaaaaaga tgaattaaag aaaatagtcg agtcatacaa cacagtatca    240

gtgctgggtg tgaccaagtc agaaggagca acaggaccaa ggctggtctc tagtttgaaa    300

ggactaaaaa accttctacc tggagtaaac cccaagacac tacaggaaac acttctggta    360

ggggcaccat gcccctcaac ggaaccaact accgaggagt actggaatgt gtgtagagca    420

gcagttggag catcaatggg atcagcaaag atcaacatgt ctcagaaggt ggtgatggga    480

gctagcgtca tcggatgggg ccaactgaac caaagcggtc caggagtgta tttcttaaac    540

actaaggaaa tagttacagc agaagggaag gtagacgaaa caagaggacc ccttgaaaga    600

acatcagctc ctctaatgag agacatatcc aggctcattc aagaaacaat agaagaagtt    660

gaaacaggag gagatccctc cttttcagta agaagtgaag gaggatcgaa gattgaagga    720

agaattgcat tctctctcca ttcagaagtg tcaacattga aaatgagaat agcactggag    780

caaaaactgg ctaaatacga gtacatggga gagaacttgt tgacacttgt caagaacacg    840

tcaatagaca ggatgcagcc ggactctgct atgatgggga agatggtgct ggaaagcctg    900

agaacgcaca ctgtttcatc tgagcagctg aatgggagga tgatcacagt acagtctcaa    960

ggattggaaa ccatagcaat atcaagtccg ttcgatgtgg aatacgatga tggatacgtt   1020

ttcacgagga tgaaagggaa ctttgttgca atcggacgag attacaaagg ggccatattg   1080

tgtttcagag aaggtcaagg aacattcttc agcggaagag gaaattggtc aggactgatg   1140

gaaaaatgtc tggttgagat gagactgtgt ccgtgcttct acagctgcac atggcaagac   1200

tacccagata agaagagtct gtacgaaaag gcaaccttcg aagccaaaca gatagtgttt   1260

gcaatgggag aaaacacagg ggtggacata agagtgaaca cagacggtga gatcggagat   1320

aaaggaatat cgctactcac aagagagaga gaagataagt acatgtcaaa ggtgtcatac   1380

gaatgcagag ttgtgagcgg aaaactggtt atgggtctgg acaagatgag cagagtagcg   1440

aaggggaact tagaagtagt tagggagaaa ggagatgata ctagtcagtc agactctttt   1500

tacgagggag ttttacaagt gggtagcatg ataggcacaa cgatggaaag cctcaaacaa   1560

caacttcaag gacctgtcgg aatctggaga gcttcagggg tgtctgctat ggagaggtgt   1620

atgaagagag gtcaaagtaa gacagtggtg gcaagtgcaa gatacacttt ccagaaaatg   1680

atggagaaga tggcaacagg tagagaagtg tcgaagtaca gcttgattat tgtcatgaga   1740

tgctgcattg gtttcacttc agaagctaac aaaagagcac tcaccaacat ctcaggaaca   1800

ggttactaca ttagtgttgc acagccaaca gtggtgaaac tagccggaga atggttgatc   1860

accccagtgg gtagatccaa aactggtgag gtgcaatatg tttcggccaa actgaagaag   1920

ggaatgacca caggaaaact agaactgatt aaaaaagcag acagatcaga tctggacaat   1980
```

```
tttcctgaac catcagcaga tgaactgctg agagagggaa cgatcgtgct aatgcaaata   2040
gggaaagaca agtggctttg cagagtaaga acaggggaca gaagagttag gacagacaca   2100
gacatacaaa gagccgaagc caagtcacaa gtcgaaaaag aagacctgat ggatgaatat   2160
ggtgtttaa                                                           2169
```

<210> SEQ ID NO 8
<211> LENGTH: 2127
<212> TYPE: DNA
<213> ORGANISM: Infectious salmon anemia virus

<400> SEQUENCE: 8

```
atggaaactc tagtaggtgg gctgctgact ggggaagatt ctctggtcag tatgtcgaat     60
gatgtgtctt gtctttacgt ttatgatgga ccaatgaggg ttttttcaca aaacgcacta    120
atgcctactt tgcaaagtgt gaagagaagt gaccagttct caaaagggaa aacaaagaga    180
ttcattatag atttgtttgg aatgaaaagg atgtgggaca tagggaacaa acatctagaa    240
gatgaaaatt tggacgaaac tgttggtgtt gcagacttag gtcttgtgaa atacctgata    300
aacaacaagt acgatgaggc agagaaaact agcttaagga agtcaatgga agaagctttc    360
gagaagtcta tgaacgaaga atttgtcgta ctgaacaaag ggaaatcagc taatgacatt    420
atctccgaca caaacgccat gtgtaaattc tgcgttaaaa actggatagt agcaacaggt    480
ttcagaggaa gaaccatgtc agacctgatt gaacaccatt tcaggtgtat gcaggggaaa    540
caagaagtga aaggatacat atggaaacat aaatacaacg agagacttaa gagaaaacaa    600
ctaagcaaag aagaagttaa gttcgacaga gaagaataca cctcaagaag cttcagacta    660
ctttcattcc tgaaaaacag cgaaagaact aagctggagc cgagagcagt gttcacagct    720
ggagtacctt ggagggcctt catcttcgtt ctagaacaga caatgctcgt cgtgaacaag    780
ttggacccaa actcagtcat ctggatggga agcgatgcca aaatcaacac aacaaactcc    840
aggataaagg agatcggaat gaagaaccaa gggcaaacac tggtaacgct tactggagac    900
aactctaagt acaatgagag catgtgccca gaagtgatga tgattttcct aagagaactt    960
gggataaagg gaccaatgct ggaagtactc gactatgctt tgtggcagtt ttctcaaaaa   1020
agtgtcaaac cagtagcacc tataaagaaa agaacaagca ggtctactgt tgtagtgaag   1080
gcggacgctg ttaacgaatg cagggacgct ttcaatgaga aggagctgga actcatacaa   1140
ggagtagagt ggatggaaga tggattcatc agagtgagaa gaggaatgtt gatgggaatg   1200
gcaaacaatg ctttcacaac ggcatctacg attgcttctt ctttcagttt cacacctgag   1260
gcagtgtaca cactacaaag ttcggatgac ttcgtgactg ggagctgtgg gagagacgta   1320
caacatgcaa gacaaagact cgaaatggct cttaaagtga gcaaagctgc aggtttgaac   1380
gtttctcaga agaagtcttt ctatgtggag gggacgactt tcgagttcaa ctctatgttt   1440
gtaagagacg ggaaagtcat ggcaaatgga ggcaactttg aaaacataac agttccaggt   1500
ggacttggac cctcaacaga tctatttgtt gttgggaaac aggcgagaaa ctccatgttg   1560
agaggaaacc tctctttcag ccaagccatg gaaatgtgca aaattggaat cacaaatgtt   1620
gaaaaggtgt actatgggaa cagaaaatac caagaactga agaacgaaat cagagaaaaa   1680
tgtggagaag agacaatgtc tatacctgag agcatgggag gtgataggaa acccaaacct   1740
tgggaacttc ctcagagttt cgatggaatt gcactcaaag aagcagtaaa caggggacac   1800
tggaaggccg ccaagtacat aaaatcttgt tgcagcattg agttcgacga ggaaggagac   1860
```

-continued

```
cagtcctggg acacgtccaa aacggcacta gtggtaatca gaaaaaacga aactgacatg   1920

agaagaagaa cagttaaaac aaggaaccct aaggacaaga tcttcaatga tgcaatgaac   1980

aaggccaaga ggatgtacga aacagtggtg gacagaaatc ctttgcttgg acttaagggg   2040

aaaggtggga gactgactgt aaaggacctg aaagcaagaa agcttatcga cgaggtggag   2100

gtgattaaga agaaaaagcg tgtttga                                       2127
```

<210> SEQ ID NO 9
<211> LENGTH: 1737
<212> TYPE: DNA
<213> ORGANISM: Infectious salmon anemia virus

<400> SEQUENCE: 9

```
atggataacc tccgtgaatg cataaaccgc aaaagaagac tacttgcact accagatgta     60

cctgaaactt cagacgcttt cctaagtgat ttgaggcatc tatacatgtg cgttgctttt    120

tgtgaccaac acagaaccac tggagacgag gcaaggttca caaacctgga actgctcgat    180

caagacgaag cgctgggtgc acagagagct ttcgaggcca aacatggaat caaaggaggg    240

tcactaggag acgtgttaga ccatgagctc aaaaaggtga ttgaattcac ttttacttca    300

ggaagtcttt acattgcaga gcaaagaaaa aggaaaactc aagcagactc catcattgta    360

tgtgtgtcag aaggactaaa tgacttcagc gtgtcacacg gtgtactaga catgggtcta    420

gtcgaaacag gagttaatgc agtaagagac ttttgcactc aaaatggaat accaatgaag    480

atcaatcagg taggatccac aagaacaccc acaccgatca gcacatgcag catttccgaa    540

cagataacaa gacagataaa cagcactatt actgacagaa aaatggagaa tgtcctggca    600

gcaattgcaa ccaaaccgga actcaaatta acacagaaag ggtgcagacc ctgcaaagaa    660

ttagaagacg aaaacgtgtt atggatggac ccgcagttct gtgaaattga tgaaagtttt    720

ccttacagag gagggccata cggaaacttc ctgcaagaat tgctgctcac aaccaacgac    780

gtagagacca acgggaaaga cagagaagag gtagtcaaga agatactgga taataaggcc    840

tttactgttg aaagcggcga atgtatcatc acactacctg acaaaatgac ttgttttggc    900

gaacaggaga agaaaaaacc agcgacatta gatgagataa gagtggcagg agagaggttc    960

gaacccagtg tgaaacctaa agcacaaaga tacggaaagc tatcagagaa gtggctagaa   1020

cttgaaaagt tcatttttac tgctagcaag acagaagtcg acacattcct ttcggtggga   1080

actgagaggc ttgagtcaat tggcgtgtgc gtaggtgctt tacacagggc gacaacaacg   1140

cggataatca gaccaatgat acagggagga aaatgctggg ggatgatgtt caagaccaag   1200

tcaaagatgg gagacacaag aaaggaagga tactgccatg caataatctt tgggaaagga   1260

gaggataaat caggccaaaa caggatgact atgatgggga agacagtata ctggcatttg   1320

agagttgtaa agtccaaagg ggactggatg gcacaacaac tgtgtgcaaa caaaagcagg   1380

atctggcaac atgacccgga gctcgtcaca gagggagtta cagtgctgat gacacctttc   1440

tcacagaaga tagctacaat tagcagatgg agagcaatga ggcttgatag catgtttcac   1500

gtctcaagtg catggcacca ttcaccagca tgtgaagctg cttcagcaat gctcaggaag   1560

tttgttgaga tagtacacgc aataaaccag aggagagact ggggtgttgt gggaagcatg   1620

gaggacatgg tcaaggaagt tgaagaaata ggcgaacatc ttcagacggc ttgtgatttt   1680

agggtacata acatgtgtaa agccttgatt cagaaaattg cagtcagtac ccaatga      1737
```

<210> SEQ ID NO 10
<211> LENGTH: 1851

-continued

```
<212> TYPE: DNA
<213> ORGANISM: Infectious salmon anemia virus

<400> SEQUENCE: 10

atggccgata aaggtatgac ttattctttt gatgtcagag acaacacctt ggttgtaaga      60

agatctaccg ctactaaaag tggtataaag atctcctaca gagaagatag aggtacttca     120

cttctccaaa aggcctttgc ggggacagat gatgaattct ggctggagct ggatcaagat     180

gtgtacgtag acaagaggac tagaaagttc cttgaggaag agaagatgaa ggacatgagt     240

cccagagtgt ctggttctgt cgctgcagca atcgaaaggt cagtggagtt cgacaacttt     300

tcaaaggaag catctgcgaa catcgagatg tcaggagagg acgaggaaga agcaggtggg     360

agtggcatgg ttgacaacaa gaggaggaac aaaggggtat ccaacatggc gtacaacctt     420

tcactgttca ttggaatggt cttccctgca atcaccacgt tcttcagcgc aatcctgtca     480

gaaggtgaaa tgagcatctg gcaaaacggg caggcaatca tgaggattct cgctttggct     540

gatgaagacg gaaagaggca aacgagaaca ggcggacaga gagtggacat ggcagatgtt     600

accaagctaa acgtggtgac agcaaacggg aaagtcaagc aggttgaagt caatttgaat     660

gacctgaagg cagctttcag acagagcaga cccaaaaggt cagactacag gaaaggacaa     720

ggatcaaagg caactgaatc aagtatttcc aaccagtgca tggctctgat tatgaagtca     780

gtgttgtcag cagaccagct gtttgcacca ggtgtgaaga tgatgaggac caatggtttc     840

aacgcatcat acactacact agcagaagga gccaacattc caagcaagta cctaaggcac     900

atgaggaact gcggaggagt tgctctagat cttatgggga tgaagaggat caagaattca     960

ccggaaggag ctaagtctaa gatcttttct atcattcaga agaaagtcag ggaaggtgt     1020

cgcactgagg agcaacggct gctgactagt gcattgaaga tcagtgatgg cgagaacaag    1080

ttccaaagga tcatggacac tctgtgcaca agctttctga ttgacccacc tagaacaacc    1140

aaatgcttca ttccacctat ctctagtctc ttgatgtaca ttcaggacgg aaattcagtg    1200

ttggcaatgg acttcatgaa gaacggagaa gatgcttgca ggatctgcag agaggcaaag    1260

ctgaaggttg gagtgaacgg cacattcaca atgtctgtgg ctagaacatg tgtagctgtg    1320

tcaatggttg caacagcatt ctgttcagca gatatcatcg agaatgcagt tcccggctca    1380

gaaaggtaca ggtcaaacat caaggcaaac acaaccaaac ccaagaagga ctcaacatac    1440

acaatccaag ggctgaggct gtccaatgtg aagtacgagg caagacctga aacatctcaa    1500

agcaacacag atcgaagctg gcaagtgaat gtcacagaca gtttcggagg gctagcggtt    1560

ttcaaccaag gcgctatcag ggagatgctt ggagatggaa catctgagac aacaagtgtg    1620

aatgtcaggg ctctggtaaa gaggatcttg aagtctgctt cagaaagaag ctcaagagct    1680

gtaaagacat tcatggttgg agaacaaggg aagtctgcaa ttgttatctc aggagtgggg    1740

cttttctcta ttgactttga aggggttgag gaggcagaga ggatcactga catgacacct    1800

gacatcgagt tcgatgagga cgatgaggag gaggaagaca ctgacatttg a             1851
```

PLASMIDS AND METHOD FOR OBTAINING VIRAL PARTICLES

FIELD OF THE INVENTION

The present invention relates to the field of medicine, veterinary medicine, molecular biology, immunology and biotechnology, specifically, to the development of vaccines and adjuvants therefor, and treatments. The field of application of this invention mainly corresponds to the fish farming industry. More specifically, this invention relates to a viral RNA expression plasmid and a method for obtaining viral particles based on said plasmids.

BACKGROUND OF THE INVENTION

Infectious salmon anemia (ISA) is a disease that mainly affects Atlantic salmon (*Salmo salar*) causing huge losses in salmon farming worldwide (1, 14). The clinical signs of this disease are the presence of pale gills, ascites, hemorrhagic necrosis of the liver, splenomegaly, congestive gut and acute anemia (14). ISA was first reported in Norway in 1984 (28), later diagnosed in Canada (4), Scotland (27), United States (18), Faroe Islands (18) and Chile (16).

The etiological agent of this disease is a packaged pleomorphic virus between 45 and 140 nm of diameter, called Infectious Salmon Anemia Virus (ISAV), belonging to the Orthomixoviridae family (8). Its genome consists of 8 ssRNA of negative polarity (ns-RNA) that encode for 10 proteins and which have Untranslated Regions (UTRs) at both ends (26).

There is a limited knowledge about the functions of each ISAV protein performs. Bioinformatics evidence indicates that segments 1, 2 and 4 would encode for dependent RNA polymerase subunits (RpRd), analogous to PB2, PB1 and PA of Influenza A virus, respectively. Segment 3 encodes for NP protein, which has been reported to have the ability to bind ssRNA (2). As for Influenza, it has been proven that these four polypeptides relate to each one of the eight viral RNA segments to form Ribonucleoprotein complexes (RNPs) (23). These eight RNP units correspond to the minimum infectious unit required to initiate a cell infection (23). Segment 5 encodes for the Fusion protein (F), which has shown to be present on the surface of the viral membrane, allowing at the first steps of the infection, the fusion of the membrane of the viral particle with the cell endosome, allowing the release of the RNPs into cell cytoplasm (3). Segment 6 encodes for hemagglutinin-esterase protein (HE), which is also present on the viral surface and whose function is to bind a sialic acid residue located in the cell receptor (15). HE protein also has receptor-destroying activity (RDE, receptor destroying enzyme), favoring the release of new viral particles emerging from the cell membrane (21). Contrary to what is observed in hemagglutinin from Influenza A virus, whose stalk region is highly kept, it has been reported that ISAV's HE protein has a highly variable region towards the carboxy terminal end and adjacent to the transmembrane region, also known as Highly Polymorphic Region (HPR) (9). This HPR region encodes for 35 amino acids and, based on its high polymorphism 30 variants have been described in Europe, North America and Chile (30, 31, 32). One theory explains this variation as a deletion phenomenon from an ancestral strain present in the longest HPR region that is called HPRO (33). The first HPRO strain was identified in Scotland in wild salmon that did not show any clinical signs of ISA, being classified as an avirulent strain (34). In contrast, those strains presenting deletions in that zone are capable of developing virulent ISA-related clinical signs and mortality. It is suggested that segment 7 encodes for non-structural proteins analogous to NS1 and NS2 of influenza A virus (19). Finally, segment 8 encodes for a transcript containing two overlapping open reading frames (ORF, Open reading Frame). ORF1 encodes for the matrix protein (M), and ORF2 encodes for M2 protein. It has been shown that M2 protein is involved in the modulation of the type-I IFN response in conjunction with the NS1 protein (12).

As regards the Influenza Virus, detailed study of the virus has been possible as a result of the development of a reverse genetics system, which allows to manipulate the virus genome, being able to determine possible causes of virulence, as well as detailed study of each one of the functions of viral proteins (13). The most widely used reverse genetics system on Influenza virus is the plasmid-based system which allows to generate recombinant viruses from cloned cDNA. ISA Virus has 8 genomic RNAs transcribed under control of RNA polymerase I and the proteins making up the ribonucleoprotein complex under the command of RNA polymerase II are expressed (10, 24).

At the date there are no reports describing a successful reverse genetics system on ISAV. A relevant difficulty in generating a reverse genetics system is having the defined promoter for RNA polymerase I, which has not yet been described for Atlantic salmon. The difficulty lies in that promoters for RNA Polymerase I are strictly species-specific, they do not have a clear genetic structure and are in the IGS region of rDNA, which are vast (6). Identification of the sequences corresponding to the promoter for Pol I and its enhancers is hard work, considering that the IGS in the *Salmo* gender varies between 15-23 kb length (5). For this reason, and in view of the need of having a promoter with RNA Pol I characteristics, here we evaluate the capacity of the 571 pb ITS-1 region (Internal Transcribed Sequences) as previously described for *Salmo salar* (Atlantic salmon) (25). It has been recently described in nematodes, through bioinformatics analysis, that the ITS-1 region contains transcription promoter motifs and regulator motifs in which their function are not been demonstrated yet (29). It is suggested in this study that in the ITS-1 region of the rDNA, there are motifs having promoter characteristics and transcription regulators that have been conserved for millions of year of evolution, differing between species of the same gender, although they suggest the making of in vitro transcription assays to prove it.

The present invention shows that ITS-1 region of the rDNA of Atlantic salmon shows transcription promoter activity, which has conserved for millions of years; however, to confirm this assertion in vitro transcription essays had to be made.

In Chile and all other salmon farmers, there is the urgent need of figure out virulence factors, pathogenesis mechanisms of ISA virus, and an efficient vaccine against the only member of the Isavirus gender, the implementation of a plasmidal reverse genetics system allowing to generate recombinant ISA virus (ISAVr) becomes a necessity. With this goal, the challenge of developing a reverse genetics system for ISAV based on plasmids and using innovative elements, such as the use of salmon's ITS-1 region which has never been described as a promoter element. A choice that turned out to be key for the success of the systems that will be described below.

DESCRIPTION OF THE INVENTION

Although this methodology has been initially developed to obtain viral particles of the ISA virus, it has been also confirmed that in other species of upper vertebrates this expression system is successful for the production of RNA molecules without any additional nucleotides on their ends, which significantly broadens the usefulness of this technique. This way, with this expression system it is possible to obtain any desired protein or RNA, in a countless different cell types. An example thereof is this system's capacity to transcribe viral RNA at 12 hpt in a human KEK 293 cell line as well as in a ST swine cell line, incubated at 37° C. (98.6° F.).

Therefore, the present invention seeks to solve the technical problem of providing a molecular genetics system allowing to obtain functional viral particles from ns-RNA. Other purpose of this invention is to provide a method for expressing autogenic or exogenic proteins to the viral particle used, as well as to express nucleic acids of the interference ARN-type.

DETAILED DESCRIPTION OF THE INVENTION

Cell Lines Used

ASK cells (www.atcc.org, CRL 2747), derived from Atlantic salmon kidney, were cultured in Leibovitz medium (L-15, Hyclone), supplemented with 50 μg/mL gentamicin), 10% bovine serum (SFB, Corning Cellgro®, Mediatech), 6 mM L-glutamine (Corning Cellgro®, Mediatech) and 40 μM β-mercaptoethanol (Gibco®, Life Technologies). RTG-2 cells (www.phe-culturecollections.org.uk, ECACC 90102529), derived from rainbow trout gonad tissue, were cultured in a minimum essential medium (MEM, Hyclone) supplemented with 50 μg/mL gentamicin, 10% SFB (Corning Cellgro®, Mediatech), 10 mM L-glutamine (Corning Cellgro®, Mediatech), 1% non-essential amino acids (Hyclone) and 10 mM HEPES (Hyclone). CSE-119 cells, derived from Coho salmon embryo (www.phe-culturecollections, ECACC 95122019) were cultured in a minimum essential medium (MEM, Hyclone) supplemented with 50 μg/mL gentamicin, 10% SFB (Corning Cellgro®, Mediatech), 2 mM L-glutamine (Corning Cellgro®, Mediatech), 1% non-essential amino acids (Hyclone). The cell lines were raised at 60.8° F., without CO2, except for CSE-119.

HEK293 cells (ATCC CRL 1573), human embryonic kidney cells, were cultured in Eagle's Minimum Essential Medium (EMEM, Hyclone), supplemented with 50 μg/mL gentamicin, 10% FBS (Corning Cellgro®, Mediatech), 10 mM L-glutamine (Corning Cellgro®, Mediatech), 1% non-essential amino acids (Hyclone) and 10 mM HEPES (Hyclone). ST cells (www.atcc.org, CRL 1746) derived from swine testicles, were cultured in Eagle's Minimum Essential medium (EMEM, Hyclone) supplemented with 50 μg/mL gentamicin), 10% FBS (Corning Cellgro®, Mediatech), 10 mM L-glutamine (Corning Cellgro®, Mediatech), 1% non-essential amino acids (Hyclone) and 10 mM HEPES (Hyclone).

Purification of ISAV Viral Particles

Virus purification was performed from 40 mL of ASK cell supernatant infected with the ISAV901_09 strain. After 14 post infection days, the cell supernatant was taken and clarified at 1000×g for 20 minutes at 39.2° F. The supernatant was then ultracentrifuged at 133,200×g for 2 hours at 4° C. (39.2° F.) and the pellet obtained was suspended in 100 μL TNE buffer overnight, at 4° C. (39.2° F.). Then, the suspension was loaded into 4 mL of a 20% w/v sucrose mattress in TNE buffer, and was ultracentrifuged at 124,200×g for 2 hours at 4° C. (39.2° F.), and, finally, the resulting pellet was re-suspended in 50 μL of TNE buffer.

Viral RNA Extraction

Viral RNA extraction (vRNA) was performed from 50 μL of purified ISAV901_09 virus, using the commercial E.Z.N.A kit. Total RNA Kit II (Omega, Bio-Tek, Inc.), according to manufacturer's instructions. The purified RNA was then quantified by measuring absorbance at 260 nm through the Nanoquant Infinite M200 pro (TECAN, Austria) equipment, and a vRNA concentration of 2.7 μg/μL was obtained. The vRNA was stored at −80° C. (−112° F.), until its use.

Amplification of the Complete 8 IASV 901_09 Genomic Segments, Bioinformatics Analysis and Primer Design.

The sequences including the non-coding 5' and 3' UTR ends of the eight genomic segments of the publications by Fourrier et al., Kulshreshtha et al., and Merour et al., (11, 17, 20), were collected. These sequences correspond to two Scottish isolates (390/98 and 982/08), one Norwegian isolate (Glesvaer/2/90), two Canadian isolates (NBISA01 and RPC NB 98-049) and a Chilean one (ADL-PM 3205 ISAV). Multiple alignment was performed using the ClustalW2 program. Based on the analysis of the alignments, the universal primers were designed to amplify the 8 complete segments, including the 5' and 3' UTR regions of any ISAV strain (Table I).

RT-PCR

The viral RNA of ISAV901_09 (7) was obtained by extraction from purified virus; the cDNA of the eight genomic segments was obtained via RT-PCR. To this effect, the SuperScript™ One-Step RT-PCR System with Taq Platinum DNA Polymerase kit (Invitrogen) was used following manufacturer's instructions. In order to obtain the cDNA of each segment in the RT-PCR reaction, the primer F (forward) (10 μM) and the appropriate R primer (reverse) (Table I) and 50 ng viral RNA, were used.

TABLE 1

Primers for amplifying the 8 complete ISAV segments

| Primer | F (forward) 5' to 3' primer | R (reverse) 5' to 3' primer |
|---|---|---|
| 1a (SEQ ID NO 11/ SEQ ID NO 12) | AGCTAAGAATGGACTTTATAT-CAGAAAACACG | AACCTTCGAAGCCAAACAGATAG |
| 1b (SEQ ID NO 13/ SEQ ID NO 14) | CAATATCAAGTCCGTTCGACGTGG | AGTAAAAAATGGACATTTTATTGATTAAAAGTATCGTC |

TABLE 1-continued

Primers for amplifying the 8 complete ISAV segments

| Primer | F (forward) 5' to 3' primer | R (reverse) 5' to 3' primer |
|---|---|---|
| 2 (SEQ ID NO 15/ SEQ ID NO 16) | AGCAAAGAACGCTCTTTAATAACC | AGTAAAAAATGCTCTTTTACTTATTAAAAAT |
| 3 (SEQ ID NO 17/ SEQ ID NO 18) | AGCAAAGATTGCTCAAATCCC | AGTTAAAATTGCTCTTTTCTTTATTTG |
| 4 (SEQ ID NO 19/ SEQ ID NO 20) | AGCTAAGATTGGCTGTTTCAAGA | AGTAAAAATTGGCTTTTTGGAAAA |
| 5 (SEQ ID NO 21/ SEQ ID NO 22) | AGTTAAAGATGGCTTTTCTAACA-ATTTT | AGTAAAAATTGGCTATTTATACAATTAATAATG |
| 6 (SEQ ID NO 23/ SEQ ID NO 24) | AGCAAAGATGGCACGATTCA | AGTAAAAAATGCACTTTTCTGTAAACG |
| 7 (SEQ ID NO 25/ SEQ ID NO 26) | AGCTAAGATTCTCCTTCTACAATGGA | AGTAAAAATTCTCCTTTTCGTTTTAAA |
| 8 (SEQ ID NO 27/ SEQ ID NO 28) | AGCAAAGATTGGCTATCTACCA | AGTAAAAAAAGGCTTTTTATCTTTTG |

Sequencing

The cDNAs of the ISAV genomic segments were cloned in the pGEMT-easy vector (Promega), following manufacturer's instructions. Three clones of each plasmid were sequenced using universal primers for promoter T7 and SP6, in addition to internal primers for each segment, as described in Cottet et al (7).

The sequencing results were analyzed using the BioEdit Sequence Alignment Editor 7.1.3 program, and to confirm the identity of the sequences, a local alignment was made using the BLAST server. In addition, a multiple alignment, using the CLUSTALW2 server between the sequences obtained from the 3' and 5' UTR ends of all the ISAV901_09 segments, was made. Once the complete sequences of the 8 segments of ISAV901_09 (with the 3' and 5' UTR ends) were obtained, they were used to synthesize the ISAV901_09 genome (Genscript Co. USA), incorporating into its ends the cleavage sites for the SapI enzyme, and, thus, avoiding errors in the subsequent cloning in the pSS-URG vector.

Design of the Universal pSS-URG Vector Plasmid

In order to have a plasmid allowing for the transcription of the ISAV vRNA, a cassette that was synthesized using advances in synthetic biology (Genscript Co.), and incorporated into the pUC57 plasmid, was designed. The new vector built was called pSS-URG (plasmid for *Salmo Salar* Universal Reverse Genetic). FIG. 1*c* shows the scheme of all of the elements required for a correct transcription of vRNAs. Arranged from left to right, it follows that: as a promoter, ITS-1 region of *Salmo salar*; the sequence of hammerhead rybozime; rybozime of the hepatitis Delta virus (δ); between the sequences of the two ribosomes are the cut sites for the Sap I distant cut enzyme (New England Biolabs), and, finally, the rabbit β-globin transcription terminator. This innovative design allows to insert any ISAV genomic segment, or any other nucleotidic sequence, without incorporating other sequences at vRNA's both ends. Then, each one of the 8 cDNAs of the complete ISAV segments were cloned in the Pss-URG plasmid. This way, a collection of plasmids called pSS-URG/1, pSS-URG/2, pSS-URG/3, pSS-URG/4, pSS-URG/5, pSS-URG/6, pSS-URG/7 and pSS-URG/8, is obtained (FIG. 1*e*).

pSS-UGR/S6-NotI-HPR and pSS-UGR/S6-EGFP-HPR Vector

A construct was designed based on the pSS-URG vector having the complete sequence (including the 3' and 5' UTR ends) in antisense and inverted from segment 6 of ISAV 901_09. As a marker, the vector has additions, in frame, within the HPR region of segment 6, exactly nine nucleotides containing the restriction site for the NotI enzyme nt 1015 5'-gtagca[GCGGCCGCA]acatct-3'nt 1.036 (SEQ ID NO 29, FIG. 2). The designed vector, called pSS-UGR/S6-NotI-HPR, was synthesized at GenScript Co., using pUC57 as basis. In order to generate the pSS-URG/S6-EGFP-HPR vector, the EGFP coding sequence was cloned into the pSS-UGR/S6-NotI-HPR vector using Not I restriction site of the HPR region (FIG. 2).

Vectors to Express PB2, PB1, PA and NP Proteins of ISAV901_09

From the ORFs of segments 1, 2, 3, and 4 of ISA virus 901_09 encoding for PB2, PB1, PA and NP, respectively, (SEQ ID NOS 7, 8, 9, 10) and which are cloned in the pGemT-easy vector, high fidelity PCR with Pfx Platinum (Invitrogen) was performed. The primers used to amplify each one of the gens are shown in Table 2, which include cutting sites for NcoI, SmaI and XhoI enzymes (New England biolabs). Cloning ORFs of PB2 and PA was made with NcoI and XhoI restriction enzymes, cloning of the ORF from PB1 was made with SmaI and XhoI restriction enzymes, and that of the ORF encoding for NP was with MluI and XbaI restriction enzymes. For the expression of PB2, PB1 and PA, the ORFs of segments 1, 2, and 3 were cloned in the pTriex3 vector (Novagen), named here PTRIEX, a commercial expression plasmid. On the other hand, for the expression of the NP protein, the ORF of segment 3 was cloned in the pCI-neo vector (Promega).

TABLE 2

Primers to amplify the PB2, PB1, PA and NP ORF of ISAV901_09 for cloning CMV vectors.

| ORF | 5' to 3' Primer F | 5' to 3' primer R |
|---|---|---|
| PB2 | NcoI-*ATGCC*ATGGACTTTATATCAGAA AACACGATCAGCG (SEQ ID NO 30) | XhoI-CCG*CTCGAG*AACACCATATTCATC CATAGG (SEQ ID NO 31) |
| PB1 | SmaI-TCC*CCCGGG*AAACTCTAGTAGGTG (SEQ ID NO 32) | XhoI-CCG*CTCGAG*AACACGCTTTTTCTTCTT AATCAC (SEQ ID NO 33) |
| NP | MluI-CGA*CGCGT*CATGGCCGATAAAGGT ATGAC (SEQ ID NO 34) | XbaI-CGC*TCTAGA*TCAAATGTCAGTGTCTTC CTC (SEQ ID NO 35) |
| PA | NcoI-*CATGCC*ATGGATAACCTCCGTGAA TGCATAAACC (SEQ ID NO 36) | XhoI-CCG*CTCGAG*TTGGGTACTGACTGCAA TTTTC (SEQ ID NO 37) |

Ex Vivo Transcription Trial, ASK Cell Transfection Kinetics with pSS-URG/Seg6-NotI Vector To test the functionality of the pSS-URG base vector, ASK cells were seeded at a density of $2.5\times10^4$ cell/$cm^2$ per well in a 24-well plate (SPL) in Leibovitz Medium (L-15, Hyclone), supplemented with gentamicin (50 μg/mL) and 10% fetal bovine serum (SFB, Hyclone) being cultured at 18° C. (64.4° F.), until reaching 80% confluence. The cells were transfected with the pSS-URG/S6-NotI-HPR vector using Fugene 6 (Promega) at a 1:6 ratio, following manufacturer's specifications. The cells were incubated at 16° C. (60.8° F.) for 3 hours, the mixture being then removed and the cells washed 2 twice with PBS, starting with transfection kinetics that is at 0, 3, 6, 9, 12 and 15 hours. From each well, at each point of the kinetics, total RNA was extracted from the cells using E.Z.N.A. Total RNA Kit II (Omega, Bio-Tek), DNA was eliminated by using RQ-DNase treatment (promega). The RNA obtained was subjected to RT-PCR using primers for the NotI restriction site and the 5'UTR end of viral segment 6 (Table 3).

TABLE 3

Primers to amplify vRNA of S6-NotI

| Primer | 5' to 3 sequences' |
|---|---|
| F S6-NotI (SEQ ID NO 38) | GTAGCAGCGGCCGCA |
| R S6-5'UTR (SEQ ID NO 39) | AGTAAAAAATGCACTTTTCTGAAACG |

cDNA was obtained through reverse transcription (RT) using the M-MuLV Reverse Transcriptase enzyme (Moloney Murine Leukemia Virus Reverse Transcriptase, 200 U/μL New England BioLabs). The reverse transcription mixture was made at a final 25 μL volume, in accordance with manufacturer's specifications. cDNA was then used to carry out a PCR reaction with DNA polymerase Paq5000 (Agilent Technologies). PCR products were visualized by electrophoresis at 90 volts for 1 hour on a 2% ethidium bromide-stained (10 mg/mL) agarose gel (FIG. 3).

Generation of Recombinant ISAV (ISAVr) Through Plasmid-Based Reverse Genetics System ASK cells were seeded at a density of $2.5\times10^4$ cell/$cm^2$ on Nunc™ Lab-Tek™ II Chamber Slide™ System plates, and then incubated for 72 hours at 18° C. (64.4° F.). The cells were transfected with Fugene 6 (Promega) 1:6, in accordance with manufacturer's specifications. As for the generation of ISAVr901_09, a total of 250 ng of a mixture of vectors PTRIEX3-PB2, PTRIEX3-PB1, PTRIEX3-PA and pCI-neo-NP and 1 μg of the total eight pSS-URG (pSS-URG/1-8) vectors. Recovery of the rISAVS6-NotI-HPR and rISAVS6-EGFP-HPR viruses was performed by replacing pSS-URG/6 with pSS-UGR/S6-NotI-HPR and pSS-URG/S6-EGFP-HPR, respectively. The cells were then incubated with 1 mL of L-15 medium, for 7 days at 16° C. (60.8° F.) (FIG. 4).

Infection of ASK Cells with $ISAVr^{S6-EGFP-HPR}$

ASK cells were seeded at a density of 2.5×10 4 cell/$cm^2$ per well, in 8-well Nunc™ Lab-Tek™ II Chamber Slide™ System plates, and were cultured at 16° C. (60.8° F.), until reaching 90% confluency. Then, the cells were washed with PBS twice, and blind passages were made with 100 μL of a 1:10 dilution of the supernatant either from passage 0 (P0) at 7 days post-transfection or from the different passages at 7 days post infection of ISAVrS6-EGFP-HPR in L-15 medium without SFB with gentamicin (50 μg/mL). The cells were incubated for 4 hours at 16° C. (60.8° F.), then washed twice with PBS and 500 μL of L-15 medium was added with 10% SFB and gentamicin (50 μg/mL), being then incubated for 7 days at 16° C. (60.8° F.). Each viral passage was obtained with this procedure every 7 days up to the fourth $ISAVr^{S6-EGFP-HPR}$ passage, in addition to P0. The supernatant of each passage was stored at −20° C., until further analysis thereof (FIG. 4).

$ISAVr^{S6-EGFP-HPR}$ Detection

RNA Extraction, RT-PCR and qRT-PCR in Real Time:

To detect $ISAVr^{S6-EGFP-HPR}$, a total RNA of 350 μL was extracted from the ASK cells' supernatant as transfected with the 12 plasmids at 7 post-transfection days ($ISAVr^{S6-EGFP-HPR}$) or supernatants from the $1^{st}$ to $4^{th}$ blind passages, with RNAv extracted from RNAv of segment 6, EGFP and Segment 6-EGFP being detected through RT-PCR.

Prior to the RT-PCR reaction, the RNA was treated with RNase-free DNase (Promega). For the reverse transcription reaction (RT), F-UTR-S6 primers (Table 1), F-S6 primers (Table 3), or EGFP primers (Table 4) were used, using the M-MLV RT enzyme (200 U/μL Promega), in accordance with manufacturer's specifications.

TABLE 4

Primers for the detection of vRNA from S6-EGFP-HPR

| Primer | 5' to 3' primer F | 5' to 3' primer R |
|---|---|---|
| S6 (SEQ ID NO 40/ SEQ ID NO 41) | TGAGGGAGGTAGCATTGCAT | AAGCAACAGACAGGCTCGAT |
| EGFP (SEQ ID NO 42/ SEQ ID NO 43) | CTGGAAGTTCATCTGCACCAC | TGCTCAGGTAGTGGTTGTC |
| S8 (SEQ ID NO 44/ SEQ ID NO 45) | GAAGAGTCAGGATGCCAAGACG | GAAGTCGATGAACTGCAGCGA |

For PCR, the GoTaq® Green Master Mix kit (Promega) and Forward (S6 or EGFP) and Reverse (S6 or EGFP) primers were used. The thermal program used was: 95° C. for 2 minutes, 35 95° C. cycles for 30 seconds, 59.1° C. for EGFP, or 54° C. for S6 or S6-EGFP, 30 seconds, 72° C. for 30 seconds, and a final extension of 72° C. for 5 minutes. In all of the cases, re-amplification of the PCR products was carried out, using the same primers. The products of the PCR re-amplification were visualized via electrophoresis on 1% (w/v) agarose gel, run at 90 V for 45 minutes, and stained with ethidium bromide (10 mg/mL).

In order to detect the number of copies of the vRNA, a qRT-PCR was carried out in real time using the absolute method as described by Munir and Kibenge (22), a standard curve being made from the pSS-URG/S8 plasmid. The RT-PCR analysis in real time was carried out on the Eco Real-Time PCR System equipment (Illumina), using the SensiMix™ SYBR® Hi-ROX Kit (Bioline), following manufacturer's instructions, using the F-S8 and R-S8 primers (Table 4). The thermal profile used to amplify the region of segment 8 was 1 initial denaturation cycle of 10 minutes a 95° C., followed by 40 amplification cycles (15 seconds at 95° C., 15 seconds at 60° C., and 15 seconds at 72° C.). Following the amplification cycles, a dissociation cycle (30 seconds at 95° C., 30 seconds at 55° C., and 30 seconds at 95° C., was carried out. This procedure was performed for passage 4 of the recombinant virus. The results obtained were analyzed on EcoStudy software.

Confocal Microscopy

On the 7th post-infection day, ASK cells infested with rISAVS6-EGFP-HPR in each passage of the recombinant virus were analyzed via confocal microscopy, using the procedure as described by Rivas-Aravena et al. (45). The fixed cells were observed using a LSM 510 confocal microscope (Zeiss), utilizing the LSM image Browser software to detect rISAVS6-EGFP-HPR by visualizing EGFP fluorescence. In addition, rISAV was detected using anti-HE monoclonal antibody (BiosChile), as was already described (45).

Tagging by Lysis Plate Trial

ASK cells were seeded at a density of 2.5x10 4 cell/$cm^2$ per well of a 12-well plate (SPL) and were incubated at 16° C. until reaching 100% confluency. The ISAVr$^{S6\text{-}EGFP\text{-}HPR}$ variant of Passage 4 was tagged. The procedure was performed as described by Castillo-Cerda et al (35).

ISAVr$^{S6\text{-}EGFP\text{-}HPR}$ Fluorescence Quantification Trial

ASK cells were seeded at a density of 2.5x10 4 cell/$cm^2$ per well, in a 48-well plate (SPL), and were incubated at 16° C. until reaching 100% confluency. Passage 4 of ISAVr$^{S6\text{-}EGFP\text{-}HPR}$ was tagged. To this effect, serial dilutions of each viral inoculum were performed using a 10-dilution factor, from $10^{-1}$ to $10^{-6}$ in L-15 medium, without FBS. The culture medium was then removed and 400 μL of viral inoculum was added to each well, and it was incubated at 16° C. for 4 hours to allow virus absorption. Subsequently, the inoculum was removed from each well, the cells were washed twice with PBS and, then, the L-15 medium was added, being supplemented with 10% SFB, 6 mM L-glutamine (Corning Cellgro®, Mediatech), 40 μM β-mercaptoethanol (Gibco®, Life Technologies), 50 μg/ml gentamicin. The plates were incubated for 7 days at 16° C. At the end of the infection, the supernatants from each well were analyzed, fluorescence being quantified using the Nanoquant Infinite M200 pro equipment (TECAN, Austria), exciting at 485 nm, and capturing the emission at 535 nm. These supernatants were also used for extracting total RNA and subsequent qRT-PCR, in real-time, to quantify the RNAv in ISAV segment 8, and for determining, this way, the number of copies of the cell culture from segment 8, as described above.

Infection Kinetics of ISAV901_09, ISAVr$^{901_09}$, ISAVr$^{S6/EGFP\text{-}HPR}$ Infections of ASK cells were carried out with the fourth passage of ISAVr$^{S6/EGFP\text{-}HPR}$, using the fourth passage of ISAVr$^{901_09}$ as control, in addition to wild ISAV901_09. For each virus isolate, an infection was carried out with a MOI of 0.01. The infection kinetics was carried out by collecting samples at 0, 2, 4 and 7 days after the infection, then a RNA extraction, DNase treatment, and then a real-time qRT-PCR were carried out, to quantify RNAv of ISAV segment 8 of each cell culture supernatant (22).

Visualization of Particles

The ASK cells were seeded as indicated above and cultured at 16° C. until reaching 90% confluence. Cells were then infected with 400 μL of a 1:10 dilution of ISAVr$^{S6/EGFP\text{-}HPR}$ virus in its 4th passage, or the 4th passage of rISAV$^{901_09}$ or wild ISAV901_09 as control. Four days after infection, the cells were fixed with 2.5% glutaraldehyde in cacodylate buffer 0.1 M at pH 7.2 for 6 hours at room temperature, and then washed with sodium cacodylate buffer 0.1 M at pH 7.2 for 18 hours at 4° C. The samples were then fixed with 1% aqueous osmium tetroxide for 90 minutes, and then washed with distilled water and stained with an aqueous solution of 1% uranyl acetate for 60 minutes. Samples were then dehydrated with washes of 20 minutes each time with a series of buffers containing acetone 50, 70, 2×95 and 3×100%. Samples were finally embedded in epon resin/acetone at 1:1 ratio overnight, and then embedded in pure epon resin which was polymerized at 60° C. for 24 hours. Thin sections (60-70 nm) were obtained in ultramicrotome Sorvall MT-5000, and then mounted on copper grids, and then stained with 4% uranyl acetate in methanol for 2 min, and then citrate for 5 min. The samples were observed with a 12 to 80 kV electron microscope Philips Tecnai (FIG. 6).

EXAMPLES

Figure 1:
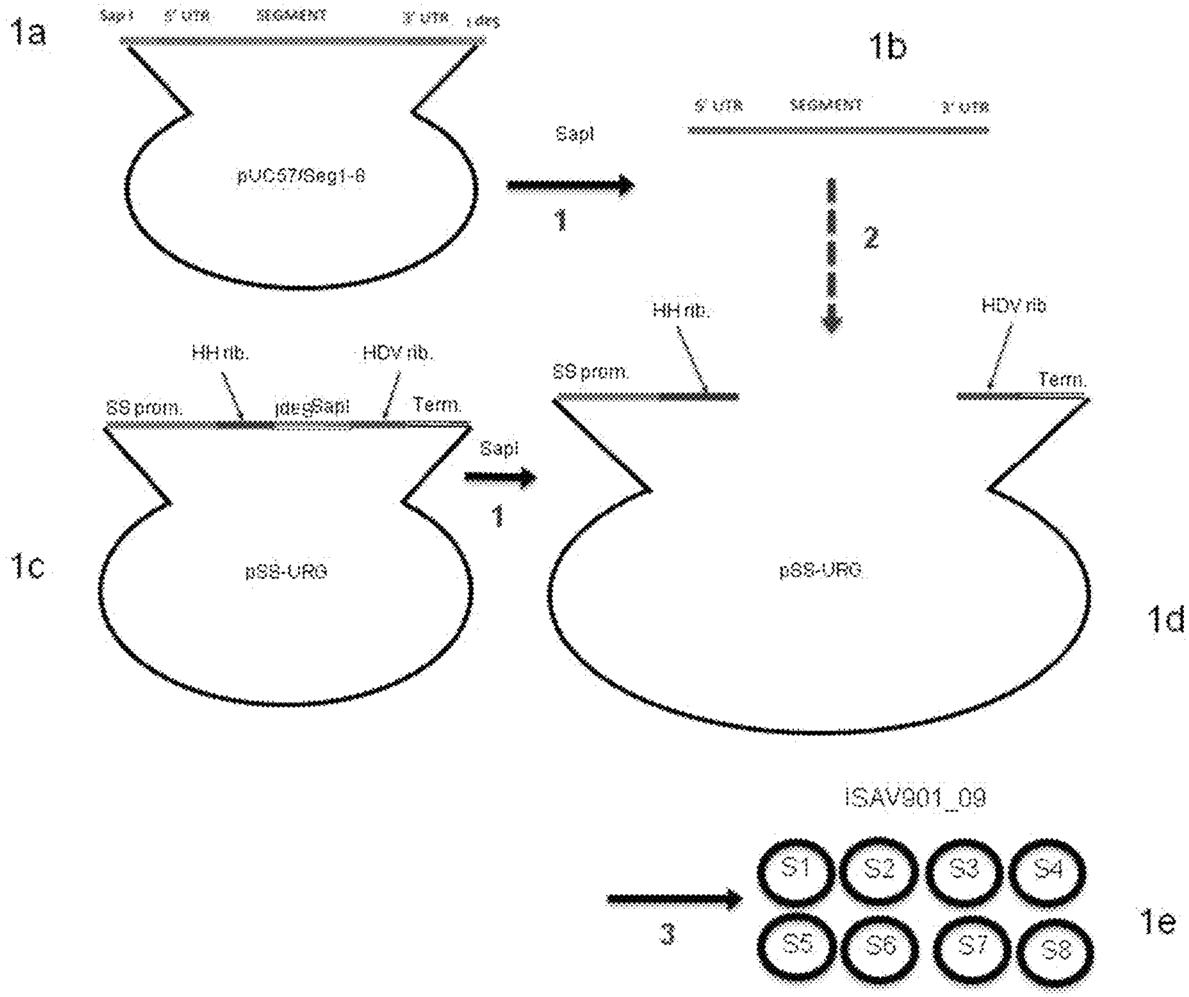
FIG. 1: Obtaining the plasmids to allow transcription of the 8 RNAv of ISAV901_09: (1) pSS-URG plasmids and the plasmid containing each of the ISAV genome segments are digested with the SapI restriction enzyme. The digestion products are visualized on a 1% agarose gel, and then purified. (2) The digested product corresponding to the ISAV genome segment and the linear pSS-URG plasmid are ligated with T4 ligase, and then this ligation is used to transform chemo-competent bacteria. (3) From the clones containing the expected recombinant plasmids, purification is carried out to confirm the correct insertion of the genome segment by sequencing.

ISAV 901_09 Strain Genome Adapted to Cell Culture

The complete genome of a virus isolate adapted to cell culture, such as ISAV 901_09 (HPR 1c), was sequenced.

Alignments between the noncoding regions (UTR) of the 5' and 3' ends of complete sequences of the six ISAV isolates, two Scots (390/98 and 982/08), one Norwegian (Glesvær/2/90), two Canadian (NBISA01 and RPC NB 98-049), and one Chilean (ADL-PM 3205 ISAV) have high conservation at the ends of each viral genome segment, allowing to design universal primers described in Table I. The primers were used to amplify the genome of the Chilean ISAV 901_09 strain. The result of sequencing the eight viral genome segments is shown in Table IV. The sizes of the eight viral segments range from 2267 bp to 906 bp for segments 1 and 8, respectively.

The sequence of the 3'UTR regions ranged from 7 nucleotides in segment 6 to 48 nucleotides in segment 3, and there were no differences in the size of each 3'UTR end previously described for the 6 genomes analyzed, except for the addition of a nucleotide at the 3'UTR end of segment 7. The sequences of the 5'UTR ends of ISAV 901_09 range from 67 nucleotides in segment 4 to 147 nucleotides in segment 3. The alignment of the UTR regions also indicates that ISAV 901_09 has a high similarity with the ISAV Glesær/2/90 strain (between 97% and 98% identity).

Universal Vector Design for ISAV Reverse Genetics

Figure 2:
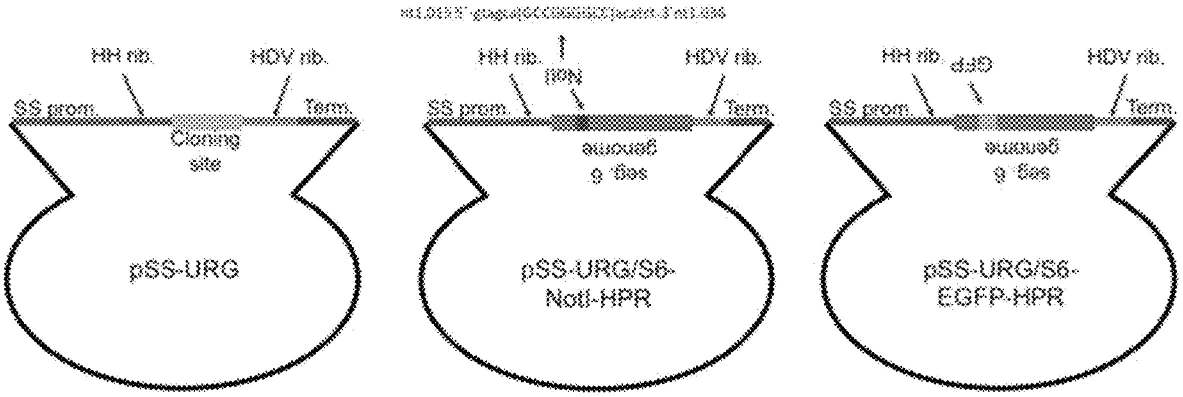
FIG. 2: Schematic design of pSS-URG, pSS-URG/S6-NotI and pSS-URG/S6-EGFP-HPR cassettes. The universal vector contains the sequence of: promoter of *S. salar* (SS prom); hammerhead ribozyme (HH rib); hepatitis virus ribozyme δ (HDV rib); rabbit β-globin transcription terminator (Term). pSS-URG/S6-Not and pSS-URG/S6-EGFP-HPR plasmids contain the cDNA of antisense and inverted segment 6, which includes 5' and 3' UTRs and their modifications; NotI restriction site or the EGFP coding sequence.

In order to achieve a vector which expresses segments of full-length viral RNA without additional nucleotides, taking advantage of advances in synthetic biology, an innovative design was made integrating elements previously used in reverse genetics of RNA viruses, such as Hammerhead ribozymes and delta (δ) hepatitis virus, together with genome elements of the *Salmo salar* species. The designed vector was called pSS-URG (plasmid for *Salmo salar* Universal Reverse Genetic). The correctly connected components contained by the vector and ordered from left to right are: As a promoter ITS-1 region of *Salmo salar*, a sequence of Hammerhead ribozyme, the ribozyme of delta (δ) hepatitis virus, and the sequences of the two ribozymes incorporate two cutting sites for Sap I enzyme (New England Biolabs), and finally incorporated as transcription terminator is rabbit beta globin terminator (FIG. 2). This vector would allow cloning, without incorporating additional sequences, any viral segment, through the use of a distant cut enzyme, such as Sap I. Thus, this study presents a vector to be the base of the reverse genetics system for the ISA virus.

Once the pSS-URG plasmid is synthesized, subcloning of the eight genome segments of ISAV was achieved from synthetic genomes using distant cut enzyme Sap I (Data not shown). In addition to cloning the eight viral segments, as a genetic marker and in order to prove that generated viruses are recombinant agents and do not correspond to a contamination of the procedure, two genetic elements were inserted in the HPR area of the universal vector containing segment 6. The first genetic variant corresponds to the insertion in the HPR area of a sequence of nine nucleotides with the cutting site for the NotI enzyme, calling this new vector pSS-URG/S6-NotI-HPR. A second genetic variant corresponds to the product of cloning the sequence which codes for EGFP using previously created NotI site, thus the new vector called pSS-URG/S6-EGFP-HPR is obtained.

Analysis of Functionality for pSS-URG Vector by Ex Vivo Transcription Trial

Figure 3:
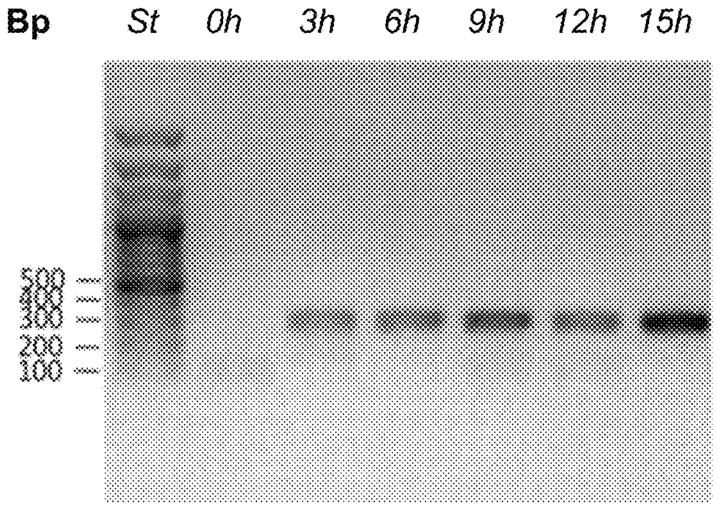
FIG. 3: RT-PCR of the 6-NotI-HPR segment from ASK salmon cells transfected with pSS-URG/S6-Not-HPR plasmids. Agarose gel electrophoresis of RT-PCR products of segment 6 at selected post transfection times. ASK cells were transfected using Fugene 6 (Promega), the plasmid used was pSS-URG/segment 6.
Figure 4:
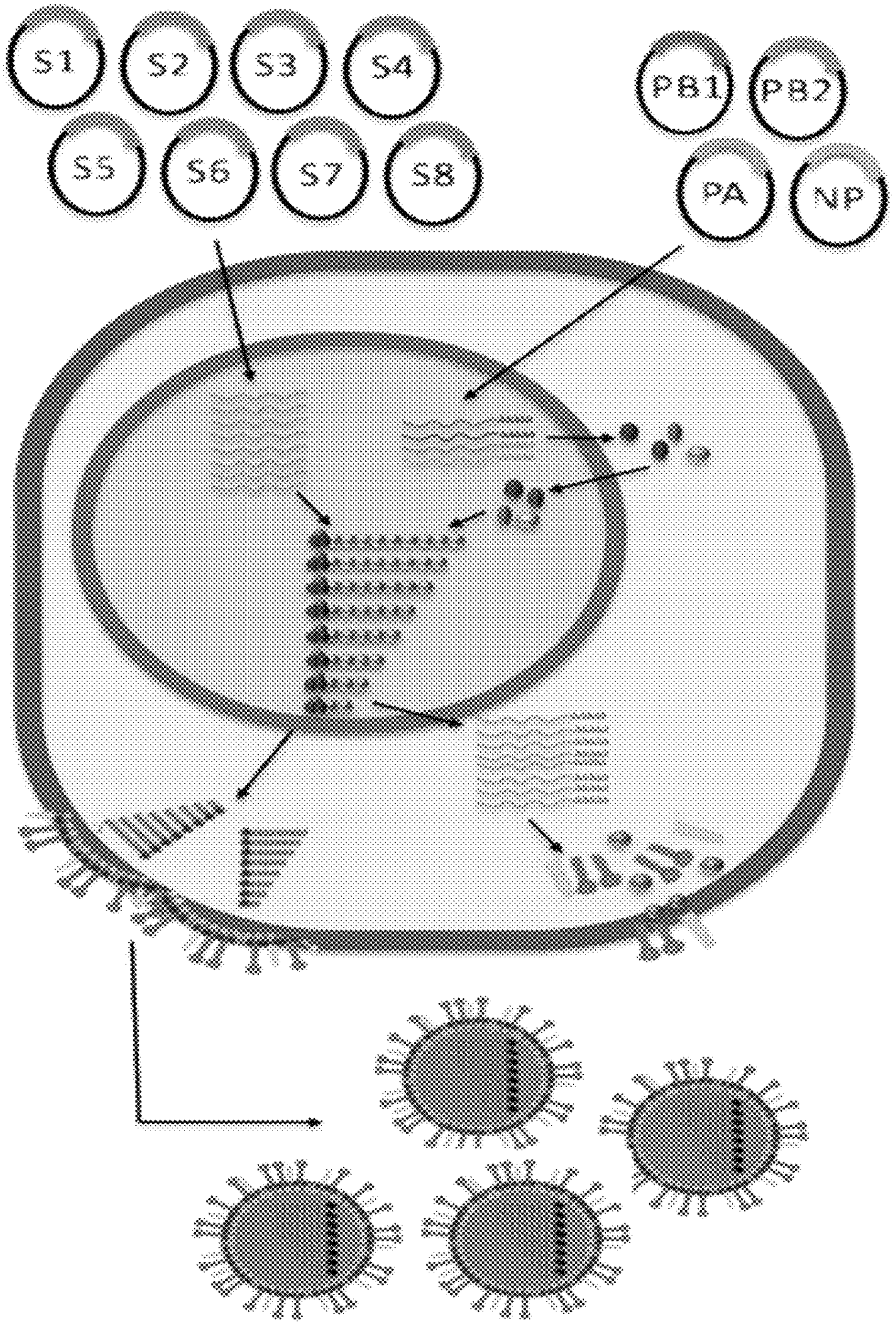
FIG. 4: Reverse genetics to obtain recombinant ISA virus: ASK cells are transfected with 8 pSS-URG/S1-8 plasmids, which allow transcription of the 8 vRNA (ISAV genome), together with 4 plasmids that allow expression of the proteins that form the cRNP (PB2, PB1, PA and NP). Co-transfection of these 12 plasmids in the same cell to allow the formation of the 8 cRNP in the nucleus, which are the minimum unit required to form an ISAV viral particle. These cRNPs allow transcription and replication of the vRNA, allowing synthesis of all proteins that form the virus and the generation of new cRNPs, thus forming recombinant viral particles.

To determine whether all the elements included in the vector allow the expression of viral RNA in salmon cells, and due to the uncertainty of functionality of the promoter suggested in ITS-1 region of *Salmo salar*, ASK cells were transfected with pSS-URG/S6-NotI-HPR plasmid in an ex vivo transcription trial. To determine the existence of a transcription process, the functionality analysis was made by detecting the RNAV at times 0, 3, 6, 9, 12 and 15 after transfection (hpt) through RT-PCR. The reverse transcription reaction was made using a single first complementary to the Not I restriction site. Surprisingly, the analysis result can display a PCR product from three hpt, which increases in intensity until 15 hpt (FIG. 3). This result would indicate that from transfected pSS-URG/S6-NotI-HPR plasmid, the cell is generating an RNA having the NotI restriction site, and therefore ITS-1 region of *Salmo salar* corresponds to a promoter element. To prove the generation of a viral RNA without additional nucleotides, a RT-PCR was carried out with specific primers for each ribozyme, the results showed that it was not possible to obtain an amplification product with primers that recognize sequences of ribozymes in any point of kinetics, indicating that generated RNA has no additional regions, such as, for example, ribozymes (data not shown).

These results suggest the use of the ITS-1 region and the inclusion in pSS-URG vector to express any type of RNA inside the cells. For example, RNA can be expressed as interfering RNA, silencing RNA or also micro RNAs.

Obtaining Recombinant ISA Virus (ISAVr)

As it has been reported for Influenza virus, the functional minimum unit of the virus corresponds to the ribonucleoprotein (RNP) complex, which consists of viral RNA that is bound by multiple copies of NP and by the viral polymerase including PB1, PB2 and PA subunits. In order to form the RNP complexes in salmon cells, ORFs of segments 1 to 4 of ISAV901_09 were cloned into expression vectors commanded by the Cytomegalovirus promoter. Thus, using the pTriEx-3 vector (Novagen), ORFs of segments 1, 2 and 4 were cloned, obtaining PTRIEX3-PB2, PTRIEX PB1, PTRIEX3-PA vectors. Besides, using the pCI-neo vector (Promega), segment 3 was cloned generating pCI-neo-NP vector (Data not shown). Transfection of these vectors into salmon cells allows expression of recombinant proteins PB2, PB1, PA and NP, respectively.

Generation of ISAVr$^{S6\text{-}NotI\text{-}HPR}$

Figure 6:
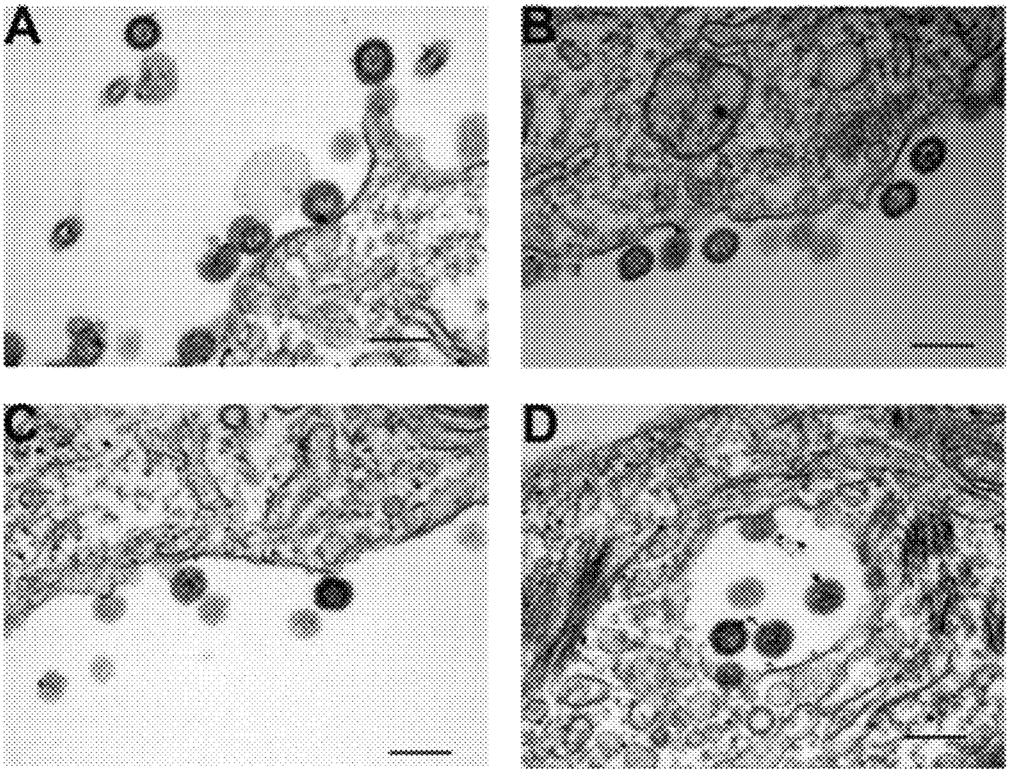
FIG. 6: Electron Microscopy Analysis of recombinant ISAV from sections of infected ASK cells. Cytoplasmic membrane with ISAV particles budding from infections with: (A) WT ISAV 901_09, (B) rISAVS6-EGFP-HPR and (C) rISAV 901_09. (D) Endosomal section showing rISAV 901_09 particles inside endosomes, which correspond to the initial steps of the fusion of viral and endosomal membranes. Bar: 200 nm.

For the generation of ISAVr S6-NotI-HPR, ASK cells were cotransfected with twelve plasmids, four of which correspond to expression vectors PTRIEX3-PB2, PTRIEX PB1, PTRIEX3 PA and pCI-neo-NP, and the remaining eight correspond to plasmids for pSS-URG reverse genetics with each of the eight genome segments of ISAV901_09 as DNA, replacing native segment 6 by Seg6-NotI-HPR. In order to amplify and determine the presence of recombinant virus, after transfection of cells, two blind passages were made in ASK cells infecting with the supernatants obtained from the previous transfections. On the one hand, the presence of RNAV of segment 6 (NotI/HPR) was detected, through RT-PCR, obtaining a product of an expected 306 bp size, both in the RNA extracted from the transfection supernatant and from the two subsequent passages, which suggests the presence of infectious viruses. The second passage supernatant was used to infect a greater amount of ASK cells. From the infected cells, which showed an obvious cytopathic effect (data not shown), the recombinant virus was visualized by transmission electron microscopy. FIG. 6 shows spherical particles similar to virus with diameters near 100 nm, which suggests that these correspond to the recombinant viruses. Therefore, it was possible to detect a recombinant ISAVr$^{S6\text{-}NotI\text{-}HPR}$ virus in infected cells, with replicative activity and reproducible cytopathic effect in passages subsequent to their generation.

Generation of ISAVr$^{S6\text{-}EGFP\text{-}HPR}$

In order to generate recombinant ISA virus containing a reporter gene, such as EGFP, in order to facilitate ex vivo monitoring and discard that results are artifactual results or contamination, ASK cells were co-transfected with twelve plasmids simultaneously: four of them correspond to expression vectors PTRIEX3-PB2, PTRIEX-PB1, PTRIEX3 PA and pCI-neo-NP; the remaining eight plasmids correspond to vectors pSS-URG/1, pSS-URG/2, pSS-URG/3, pSS-URG/4, pSS-URG/5, pSS-URG/7 and pSS-URG/8; also incorporating segment 6 with vector pSS-URG/S6-EGFP-HPR; the virus which contains EGFP in the HPR area of the protein is called ISAVr$^{S6\text{-}EGFP\text{-}HPR}$.

To determine whether recombinant viral particles were generated after transfection, the culture supernatant (passage 0, P0) was analyzed 7 days after transfection (dpt). For this purpose, it was initially detected by RT-PCR RNAv of Segment 6, as well as the EGFP coding sequence in a second PCR product, and finally an area containing both part of Segment 6 and the EGFP. The results showed that RT-PCR products for Segment 6 have a different migration distance of the PCR products for the native virus (~300 bp) and the recombinant virus having EGFP in the HE protein (1,000 bp). The RT-PCR of the EGFP coding sequence has a ~500 bp product, which is not observed in the native virus analyzed. For RT-PCR of S6-EGFP, an amplification product of ~800 bp was obtained for the recombinant virus as expected.

Infectivity of ISAVr$^{S6\text{-}EGFP\text{-}HPR}$ in ASK Cells

To determine whether the supernatant of ASK cells transfected with twelve plasmids indeed contains the viral variant ISAVr$^{S6\text{-}EGFP\text{-}HPR}$ with the characteristics of an infectious agent, EGFP fluorescence was used as a reporter. The ASK cells infected with the supernatant that would contain the first progeny ISAVr$^{S6\text{-}EGFP\text{-}HPR}$ were analyzed under confocal microscope 7 days after infection. The results show that it is possible to visualize cells emitting green fluorescence attributable to EGFP, corresponding to the first passage of the ISAVr$^{S6\text{-}EGFP\text{-}HPR}$ virus. Distribution of the EGFP mark is found mainly in the cytoplasm and towards the plasma membrane, fluorescence being not observed in the cell nucleus. To confirm that the supernatant of transfected cells (passage 0) contains the ISAVr$^{S6\text{-}EGFP\text{-}HPR}$ virus with lytic capacity, a lysis plaque trial was carried out on ASK cells. The result of the lysis plaque trial showed that the recombinant virus has the ability to generate lysis plaques like the wild virus, obtaining a virus titre in the order of $1\times10^4$ PFU/m L.

Stability of ISAVr$^{S6\text{-}EGFP\text{-}HPR}$

Subsequently, the ability of this recombinant virus to maintain infectiousness and fluorescence was assessed in cell culture. Four blind passages of infection in ASK cells were carried out with 7-day gaps. Then, in each supernatant of the recombinant virus passages, a RT-PCR was carried out to detect RNAv both of Segment 6 and of the coding sequence for EGFP, and a region of the EGFP-S6 hybrid sequence. The result made possible to visualize a PCR product of 500 bp EGFP and EGFP-S6 hybrid sequences of 800 bp, indicating the presence of segment 6 containing the EGFP gene in all supernatants analyzed. The PCR product of segment 6 shows a 300 bp product in the supernatant of infected ASK cells with ISAV901_09 wild virus, as expected, in contrast to the 1,000 bp of the PCR product obtained in each of the four passages of ISAVr$^{S6\text{-}EGFP\text{-}HPR}$ virus, whose larger size is the result of having incorporated the EGFP gene in segment 6.

To determine that each of the four passages not only had a virus with infectivity, but also was capable of fluorescing, indicating the correct folding of HE with EGFP in the HPR area, an analysis was carried out by confocal microscopy in infected ASK cells. Confocal microscopy showed cells that emit green fluorescence in all passages analyzed, increasing in each passage the abundance of fluorescent cells. These results suggest that the region of the HE protein elected to incorporate EGFP is not affected by the incorporation of this ORF, thus allowing the generation of a chimeric recombinant ISA virus capable of replicating, infecting and spreading in multiple passages without losing the ability to fluoresce. Titration of the fourth blind passage made to ISAVr$^{S6\text{-}EGFP\text{-}HPR}$ virus by qRT-PCR in real time resulted in a titre of $3.63\times10^6$ copies Seg 8/mL and a value of $6.5\times10^5$ PFU/mL obtained by lysis plaque trial, showing a lysis plaque size similar to that observed after conducting plaque trial on ISAV901_09 wild virus.

Infectivity of ISAVr$^{S6\text{-}EGFP\text{-}HPR}$ in Salmonid Cell Lines

In order to determine whether by incorporating a sequence in the HPR area of the ISAVr$^{S6\text{-}EGFP\text{-}HPR}$ virus, this acquires the ability to infect other salmonid species or lose infectivity in permissive cells (ASK cells), an infection kinetics was carried out in RTG-2, CSE-119 and ASK cells. The ex vivo trial was conducted for 7 days using the fourth passage of the fluorescent recombinant virus and compared to the ISAV901_09 wild virus, and the fourth passage of a wild recombinant virus generated for this trial rISAV$^{901_9}$ (MOI of 0.01). The analysis at 0, 2, 4 and 7 dpi by qRT-PCR quantifying the number of copies of segment 8 in each supernatant showed that none of the three viruses analyzed had the ability to replicate in RTG-2 cells or in CSE-119 cells.

In contrast, the infection kinetics carried out on ASK cells showed that initially the ISAV 901_09 virus has a larger number of copies than recombinant viruses, rISAV$^{901}$ and rISAV$^{S6\text{-}EGFP\text{-}HPR}$. On the second day after infection, however, an increase occurs in the number of copies of the recombinant viruses, reaching titres near 1,000 segment 8/mL, with values similar to the wild virus. These results suggest that the incorporation of EGFP in the HPR area of HE protein does not alter the replicative behavior of the fluorescent recombinant virus in ASK cells, and does not extend the host range at least in the ex vivo trials in RTG-2 cells or in CSE-119 cells.

These results can lead to the conclusion that it is possible to incorporate into the pSS-URG plasmid a sequence encoding both for a viral protein and for an exogenous or chimeric protein, thus achieving the generation of a modified or chimeric recombinant ISA virus; these modifications would not alter or affect its infectious or propagation characteristics.

Functionality of pSS-URG Plasmid in Salmon, Swine and Human Cell Lines

To determine the ability of the pSS-URG/S6-NotI-HPR vector for transcribing segment 6 as RNAv, it was transfected into ASK cells using Fugene 6 (Promega) at a 1:6 ratio and according to manufacturers' specifications. 0 hpt is considered as the time when adding the transfection mix to the cells. The initial incubation takes place for 3 hours at 16° C. F. Once the incubation time had elapsed, the transfection mix was removed and the cells were washed twice with PBS, this being a 3-hpt time. At each point of the transfection kinetics, which occurs at 0, 3, 6, 9, 12 and 15 hpt, the cells are removed for extraction of total RNA, possible contaminating DNA was removed with DNase I. With the RNA obtained, RNAv of segment 6 NotI was detected by RT-PCR using specific primers for segment 6 NotI. The analysis allows to observe a PCR product of expected 306 bps size from 3 hpt, which increases in intensity until 15 hpt (FIG. 3). Therefore, it is proved that the pSS-URG plasmid is functional.

Figure 5:
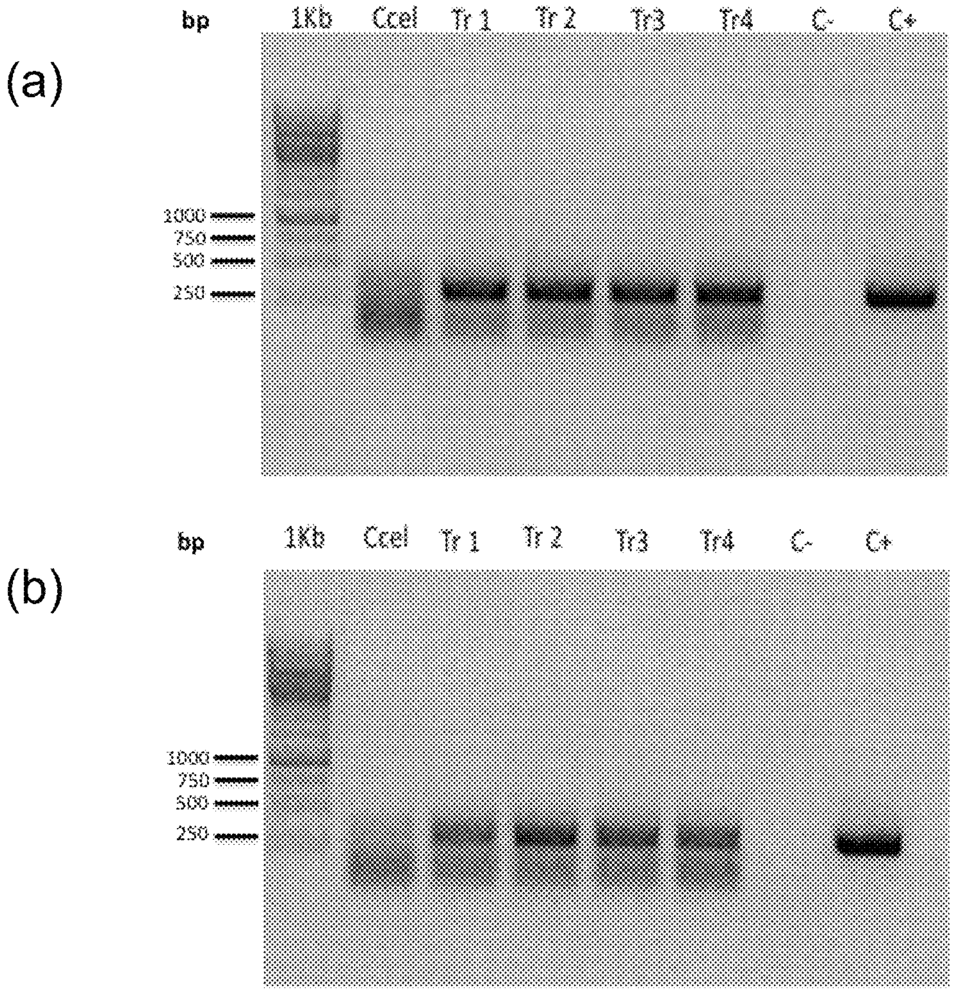
FIG. 5: RT-PCR of 6-NotI-HPR segment from ST swine cells (a) and HEK-293 human cells (b), both transfected with pSS-URG/S6-NotI-HPR plasmid using Fugene 6 (Promega). Agarose gel electrophoresis of RT-PCR products of segment 6 at selected post transfection times.

Surprisingly, the ability to transcribe the viral RNA is not restricted to salmon cells cultured at 16° C. Using the same procedure (with incubations at 37° C.), but conducted only at 12 hpt, functionality was observed in human cell line HEK 293 and swine cell line ST, incubated at 37° C. (FIG. 5). This is reflected in obtaining a RT-PCR product of the expected size which allows to conclude that the vector is functional in salmon cell lines incubated at 16° C. and mammal cell lines incubated at 37° C., being this a tool that would allow the expression of any RNA in cells or tissues of vertebrate animals, whether cold-blooded or warm-blooded.

ISAVr$^{S6\text{-}EGFP\text{-}HPR}$: Correlation Between the Number of Viral Copies and Measured Fluorescence Since the ISAVr$^{S6\text{-}EGFP\text{-}HPR}$ virus has similar characteristics to the wild virus when infecting ASK cells, and also has the advantage of monitoring the infection by incorporating EGFP as reporter, the goal is to determine whether there is correlation between the viral load and fluorescence in the supernatant of infection caused by this recombinant virus. The analysis carried out on serial dilutions of fluorescent recombinant virus through qRT-PCR and fluorescence quantitation established that there is a direct relationship showing an increased fluorescence detected when the viral titer of the solution increases, showing a fluorescence intensity of 500 units/mL for a titer of $2\times10^6$ copies/mL.

What is claimed:

1. A method of obtaining viral particles, the method comprising:

a) transfecting each of a plurality of fish cells with a set of plasmids, which express: SEQ ID NO 7, SEQ ID NO 8, SEQ ID NO 9, and SEQ ID NO 10, wherein one of SEQ ID NOs 7, 8, 9, or 10 is cloned individually in each of the plasmids;

b) once the cells are transfected in step a), co-transfecting the fish cells of step a) with a set of eight plasmids: pSS-URG/1, pSS-URG/2, pSS-URG/3, pSS-URG/4, pSS-URG/5, pSS-URG/6, pSS-URG/7, and pSS-URG/8, each plasmid having:

a promoter sequence of *Salmo salar* internal transcribed sequences (ITS-1) region;

a hammerhead ribozyme (HH rib) sequence;

one coding sequence of infectious salmon anemia virus (ISAV) inserted in a cloning site sequence, wherein each pSS-URG/1 to 8 plasmid includes a different coding sequence of ISAV;

a hepatitis δ virus ribozyme sequence; and a rabbit β-globin transcription terminator sequence; and c) obtaining recombinant viral particles resulting from steps a) and b).

2. The method of claim 1, wherein the fish cells in steps a), b), and c) are cultured at 15-20° C.

3. The method of claim 1, wherein the recombinant viral particles express nucleic acids of single-stranded chimeric RNA of the ISAV.

4. The method of claim 1, wherein the recombinant viral particles express autogenous or exogenous proteins of the ISAV.

5. The method of claim 1, wherein the set of eight plasmids includes at least one recombinant plasmid comprising: a skeleton obtained from a pUC57 plasmid in which genomic sequences of viruses expressed as RNA can be introduced, the sequences being selected from a group consisting of: a promoter sequence of *Salmo salar*; a hammerhead ribozyme (HH rib) sequence; a cloning site sequence; a hepatitis δ virus ribozyme sequence; and a rabbit β-globin transcription terminator sequence.

6. The method of claim 1, wherein the promoter sequence of *Salmo salar* is SEQ ID NO 1.

7. The method of claim 1, wherein the HH rib sequence is SEQ ID NO 2.

8. The method of claim 1, wherein the cloning site sequence is SEQ ID NO 3.

9. The method of claim 1, wherein the hepatitis δ virus ribozyme sequence is SEQ ID NO 4.

10. The method of claim 1, wherein the rabbit β-globin transcription terminator sequence SEQ ID NO 5.

11. The method of claim 1, further comprising: cloning genetic sequences of an animal, plant, protist, fungal, bacterial, or viral origin into the plasmids using distant cut restriction enzyme SapI.

12. A set of expression plasmids including SEQ ID NOs 7, 8, and 9, wherein each of SEQ ID NOs 7, 8, and 9 is cloned individually in each expression plasmid.

13. An expression plasmid including SEQ ID NO 10.

* * * * *